(12) United States Patent
Pattnaik et al.

(10) Patent No.: US 11,062,439 B2
(45) Date of Patent: Jul. 13, 2021

(54) AUTOMATING MICROFACIES ANALYSIS OF PETROGRAPHIC IMAGES

(71) Applicant: Halliburton Energy Services, Inc., Houston, TX (US)

(72) Inventors: Sonali Pattnaik, Houston, TX (US); Songhua Chen, Katy, TX (US); Wei Shao, Conroe, TX (US); Adly Helba, New Cairo (EG)

(73) Assignee: Halliburton Energy Services, Inc., Houston, TX (US)

( * ) Notice: Subject to any disclaimer, the term of this patent is extended or adjusted under 35 U.S.C. 154(b) by 72 days.

(21) Appl. No.: 16/580,595

(22) Filed: Sep. 24, 2019

(65) Prior Publication Data
US 2021/0090239 A1     Mar. 25, 2021

(51) Int. Cl.
*G06T 7/00*     (2017.01)
*G06N 3/08*     (2006.01)
*G06K 9/62*     (2006.01)
*G06T 7/174*     (2017.01)
*G06T 7/11*     (2017.01)

(52) U.S. Cl.
CPC .......... *G06T 7/0004* (2013.01); *G06K 9/6223* (2013.01); *G06N 3/088* (2013.01); *G06T 7/11* (2017.01); *G06T 7/174* (2017.01); *G06T 2207/10056* (2013.01); *G06T 2207/20081* (2013.01); *G06T 2207/20084* (2013.01); *G06T 2207/30181* (2013.01)

(58) Field of Classification Search
CPC ......... G06T 7/0004; G06T 7/11; G06T 7/174; G06T 2207/20081; G06T 2207/30181; G06T 2207/20084; G06T 2207/10056; G06N 3/088; G06K 9/6223
See application file for complete search history.

(56) References Cited

U.S. PATENT DOCUMENTS

| 8,909,508 | B2 * | 12/2014 | Hurley ..................... G06T 7/11 703/9 |
| 9,626,771 | B2 | 4/2017 | Mezghani et al. |
| 2007/0133866 | A1 | 6/2007 | Chang et al. |
| 2010/0111396 | A1 * | 5/2010 | Boucheron .......... G06K 9/6231 382/133 |

(Continued)

FOREIGN PATENT DOCUMENTS

CN     107545577 A     1/2018

OTHER PUBLICATIONS

Ng, H. P., et al. "Medical image segmentation using k-means clustering and improved watershed algorithm." 2006 IEEE southwest symposium on image analysis and interpretation. IEEE, 2006. (Year: 2006).*

(Continued)

*Primary Examiner* — Bobbak Safaipour
(74) *Attorney, Agent, or Firm* — Conley Rose, P.C.; Rodney B. Carroll

(57) ABSTRACT

Disclosed herein are methods and systems that determine a microfacies or a microfacies characteristic of a sample of a subterranean formation based on a segmented image of a petrographic image of the sample, wherein the segmented image is derived from the petrographic image using a machine-learning algorithm.

26 Claims, 9 Drawing Sheets

(56) References Cited

U.S. PATENT DOCUMENTS

2011/0015909 A1 1/2011 Zhao
2018/0106917 A1 4/2018 Osypov et al.

OTHER PUBLICATIONS

Foreign Communication from Related Application—International Search Report and Written Opinion of the International Searching Authority, International Application No. PCT/US2019/053543, dated Jun. 22, 2020, 13 pages.

Ma, Zheng et al., "Image analysis of rock thin section based on machine learning," the Society of Exploration Geophysicists and the Chinese Geophysical Society, 2017, pp. 844-847.

Xia, Xide, et al., "W-Net: A Deep Model for Fully Unsupervised Image Segmentation," Nov. 22, 2017, pp. 4321-4333.

Bukharev, Aleksander, et al., "Automatic Analysis of Petrographic Thin Section Images of Sandstone," Sep. 2018, 1 page plus cover, MIPT Center for Engineering and Technology.

Shi, Jianbo, et al., "Normalized Cuts and Image Segmentation," IEEE Transactions on Pattern Analysis and Machine Intelligence, Aug. 2000, pp. 888-905, vol. 22, No. 8, IEEE.

Achanta, Radhakrishna, et al., "SLIC Superpixels," EPFL Technical Report 149300, Jun. 2010, 15 pages.

Arns, Christopher H., et al., "Accurate estimation of transport properties from microtomographic images," Geophysical Research Letters, Sep. 1, 2001, pp. 3361-3364, vol. 28, No. 17, American Geophysical Union.

Chevitarese, Daniel, et al., "Transfer Leaning Applied to Seismic Images Classification," Oct. 1, 2018, Search and Discovery Article #42285, 14 pages, Datapages.

Lokier, Stephen W., et al., "The petrographic description of carbonate facies: are we all speaking the same language?," Sedimentology, 2016, pp. 1843-1885, vol. 63, International Association of Sedimentologists.

Zhao, Tao, "Seismic Facies Classification Using Different Deep Convolutional Neural Networks," Geophysical Insights, 2018, pp. 2046-2050, SEG International Exposition and 88th Annual Meeting.

* cited by examiner

AUTOMATING MICROFACIES ANALYSIS OF PETROGRAPHIC IMAGES

TECHNICAL FIELD

This disclosure relates generally to the analysis of petrographic images on a microscopic scale.

BACKGROUND

Exploration for minerals and hydrocarbons is based upon the geological study, observation, and interpretation of the rocks contained in subterranean (geological) formations. During exploration, a representative sample (e.g., a core sample, a core plug, or drill cuttings) of a subterranean formation can be obtained, and petrographic analysis of microscopic petrographic images obtained from the sample is an invaluable way to identify or determine the nature of different minerals, other components, and features (e.g. texture and fabric) of the rock that is in the subterranean formation.

Petrographic images are made by cutting a thin slice of the physical sample (e.g., a thin slice of rock), optionally treating the slice for imaging, and capturing the petrographic image of the slice. Microfacies analysis is usually performed manually by a human geoscientist that visually inspects the petrographic images one-by-one in order to determine the microfacies and microfacies characteristics that are displayed in the petrographic image. Manual analysis is time-intensive, due to the human-based observations, especially for large sets of petrographic images. Moreover, manual analysis is subjective, again due to human-based observations that are limited to an individual's experience in microfacies analysis; thus, processing large sets of petrographic images can take an unacceptably long period of time if performed by one geoscientist, or can be subject to different subjective interpretations if multiple geoscientists are used to interpret a large set of petrographic images.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

DETAILED DESCRIPTION

Figure 1:
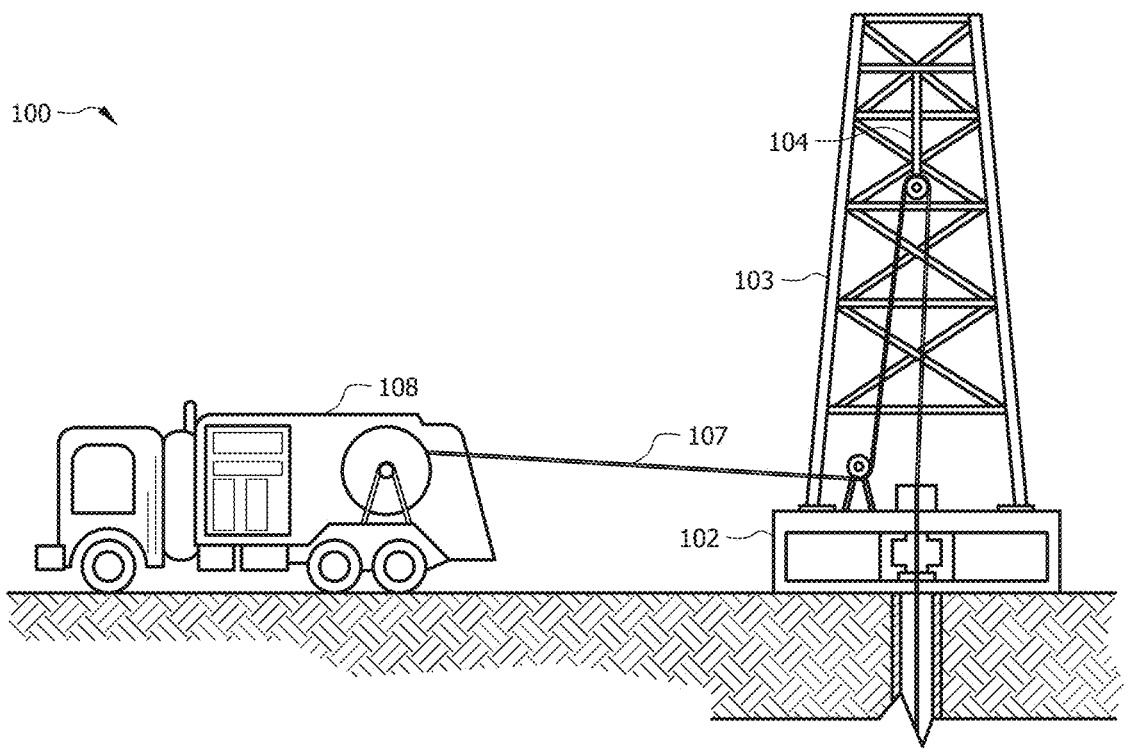
FIG. 1 is a cross-sectional view of a wellbore environment.

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

A thin section sometimes refers to a physical slice of a sample of rock that is obtained from a subterranean formation by any technique known for obtaining the sample, such as by core sampling while wireline logging, by core sampling while drilling a wellbore, or by collecting drill cuttings obtained when drilling a wellbore. The thin section may have a length and width that are substantially greater than a thickness of the thin section. Exemplary and non-limiting values for the average thickness of a thin section can range from greater than 0 micron to about 100 micron; alternatively, can range from about 1 micron to about 100 micron; alternatively, can range from about 10 to 70 microns; alternatively, can range from about 20 to 60 microns; alternatively, can range from about 30 to 50 microns; alternatively, the thickness of a thin section can be about 1, 2, 3, 4, 5, 6, 7, 8, 9, 10, 15, 20, 25, 30, 35, 40, 45, 50, 55, 60, 65, 70, 75, 80, 85, 90, 95, or 100 microns.

The terms petrographic image and thin-section image may refer in some instances to a two-dimensional digital image of the physical thin section, each image having a pixel resolution, such as but not limited to, 1400 pixels by 900 pixels.

The term cement is sometimes used to refer to the post-depositional crystalline, transparent, and/or opaque mineral material that either i) occluded completely or partially the inter- and intra-grains (particles) pore spaces or ii)

replaced completely or partially the inter- and intra-grains pre-existing (original) material, formed between sedimentary grains of a rock.

The term facies may encompass one or more chemical, mineralogical, physical, and/or biological characteristics of a rock that distinguishes the rock from another rock.

The term facies characteristic may refer to one of the chemical, mineralogical, physical, biological, or geometrical characteristics the define the facies of a rock.

The term microfacies may refer to a particular category of lithofacies that is defined by the petrographic and petrophysical characteristics of a rock that distinguishes the rock from the petrographic and petrophysical characteristics of other rocks. A microfacies may be defined by the rock's petrographic and petrophysical characteristics, such as the composition, texture, fabric, pore system, and structure of the rock.

The terms matrix and matrix material may refer to grains and solids present in space between grains (e.g., inter-grain mud-size material and cement).

The term unsupervised in the context of machine-learning algorithms may refer to machine-learning algorithms that find previously unknown patterns in a data set without pre-existing labels being assigned to data in the data set.

The term supervised in the context of machine-learning algorithms may refer to machine-learning algorithms that utilize pre-existing labels being assigned to data in the data set being analyzed.

Disclosed herein are methods and systems that determine a microfacies or a microfacies characteristic of a sample of a subterranean formation, based on a segmented image/images that is derived from a petrographic image/images of the sample using a machine-learning algorithm.

Subterranean formations can contain rocks of many types and fluids (e.g., hydrocarbons, mud, water, brine) in pore spaces of the rocks. The ability to identify the microfacies and/or characterize the microfacies characteristics of the rock is valuable to understand the nature and content of a reservoir contained in the subterranean formation. The utilization of segmented images provided by machine-learning algorithms in the disclosed methods and systems improves the technical field of petrographic image analysis at least by i) automating observation of the microfacies and/or microfacies characteristics of the rock and ii) making the analysis more objective than human-based analysis, which improves the uniformity of microfacies and/or microfacies characteristic identification, especially for large sets of petrographic images. Moreover, the use of segmented images provided by machine-learning algorithm(s) to determine a microfacies or a facies characteristic involves the transformation of the petrographic images into segmented images, which enables the disclosed computer system to interpret the pixels in a high volume of segmented images, which in turn makes identification of the microfacies characteristics that are valuable in understanding the content of a reservoir contained in a subterranean formation faster and more objective. Further, the use of segmented images provided by machine-learning algorithm(s) to determine a microfacies or a microfacies characteristic involves automating microfacies analysis through the use of specific rules, in that, the algorithms are limited to machine-learning algorithms, the algorithms can be supervised or unsupervised which imposes restrictions on the way data is used, each type of machine-learning algorithm has specific rules by which the machine-learning is accomplished, and use of convolutional neural networks involves layered software. Further still, the training and data augmentation techniques (image cropping, rotation of images, adding noise to image, light variation, etc.) improve the semantic segmentation results of the machine-learning algorithms. Yet further still, the post-processing techniques disclosed herein improve the semantic segmentation results of the machine-learning algorithms, e.g., because the post-processing compensates for over-segmentations in the segmented image provided by a convolutional neural network.

FIG. 1 is a schematic view of a wellbore environment 100 by which a sample may be obtained from a subterranean formation 101. The wellbore environment 100 includes a platform 102 that supports a derrick 103 having a pulley 104 for centering a wireline tool 105 into the wellbore 106. The wireline tool 105 is attached to a wireline 107 that is deployed from a wireline truck 108. The wireline tool 105 includes a core sampling device that is configured to gather one or more core samples from the subterranean formation 101 via the wellbore 106. The wireline tool 105 can be inserted and removed to and from the wellbore 106 any number of times so as to obtain any number of samples of the subterranean formation 101, for example, according to desired depths in the wellbore 106.

Figure 2:
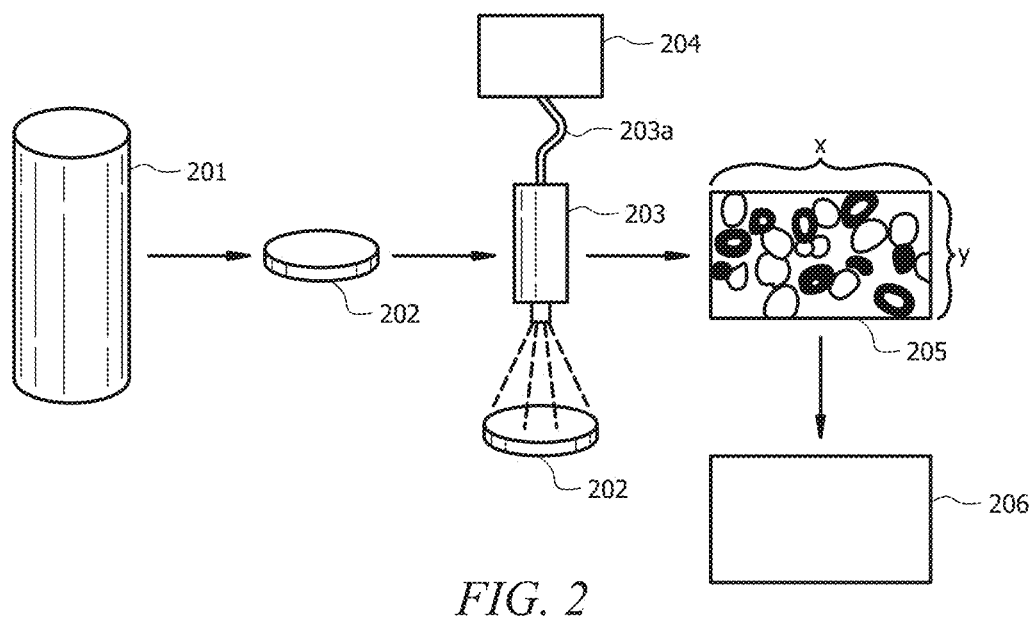
FIG. 2 is a schematic view of the conversion of a sample of a subterranean formation to a segmented image, including an embodiment of the disclosed computer system.

FIG. 2 is a schematic view of how a sample is converted to a segmented image according to this disclosure. In FIG. 2, the sample is a core sample 201 which is cylindrical in shape. In practice, the sample can have any shape and the present disclosure is not limited to cylindrically shaped samples. A thin section 202 can be prepared from the core sample 201, for example, by using a stone saw to cut the thin section 202 from the core sample 201. The thin section 202 can then be digitally imaged by an image capture device 203 that is connected (e.g., via a communication link or network 203a) to a computer system 204. In embodiments, the image capture device 203 can be a high-resolution polarized microscope, such as confocal microscope. In some embodiments, the thin section 202 can be treated before imaging, such as by smoothing the thin section 202, polishing the thin section 202, adding one or more dyes to the thin section 202, or a combination of techniques. The result of digital image capture is the petrographic image 205. As explained in detail below, the computer system 204 is configured to produce the segmented image 206 from the petrographic image 205 by performing a machine-learning algorithm on the petrographic image 205.

The computer system 204 has at least one computer device having a processor, at least one datastore, at least one non-transitory information storage medium, and software stored on the storage medium for executing one or more of the functions described herein. The computer device(s) of the computer system 204 can be embodied as one or more desktop computers, one or more laptop computers, one or more smartphones, one or more tablets, one or more external datastores (e.g., an external hard drive or flash memory), one or more servers, one or more virtual computers in the cloud, one or more big data platforms (e.g., MICROSOFT AZURE, SAP CLOUD PLATFORM, and ORACLE CLOUD INFRASTRUCTURE), or a combination thereof. When multiple computer devices are present in the computer system 204, the computer devices can be connected for communication of data (e.g., the petrographic image 205 and segmented image 206) via any number and any configuration of communication links and/or networks, such as a wireless connection (e.g., Wi-Fi, Bluetooth) and/or a wired connection (e.g., Ethernet, USB) on a LAN or WAN that is in turn networked with a VPN, cloud network, the Internet, or a combination thereof.

In some embodiments, the computer system 204 can be located at a single physical location, such as a well site;

alternatively, components of the computer system 204 can be distributed among two or more physical locations, such as a desktop or laptop computer at the location where the petrographic image 205 is generated and a big data platform in one or more other locations where the petrographic image is segmented using a machine-learning algorithm.

Software on one or more non-transitory information storage medium may configure the computer system 204 to produce at least one petrographic image for the thin section 202, i.e., the petrographic image 205 in FIG. 2 (also called the thin-section image), which is the two-dimensional digital image of the thin section 202. The computer system 204 is configured to produce the petrographic image 205 with a resolution of X pixels by Y pixel, where X and Y can be any resolution of pixels suitable for petrographic imaging. An exemplary and non-limiting resolution is X=1400 pixels and Y=900 pixels. The computer system 204 can include one or more datastore in which the petrographic image 205 is stored.

Geoscientists typically visually analyze the petrographic image 205 to determine various characteristics of the rock. The disclosed method and system automate the analysis through the use of a machine-learning algorithm.

In embodiments, software on one or more non-transitory information storage medium may configure the computer system 204 produce the segmented image 206 by performing a machine-learning algorithm on the petrographic image 205. In some embodiments, the machine-learning algorithm can be supervised; alternatively, the machine-learning algorithm can be unsupervised. The machine-learning algorithm can be any machine-learning algorithm suitable for microfacies analysis of the petrographic image 205. Embodiments of the machine-learning algorithm include an unsupervised K-means clustering algorithm, a supervised clustering algorithm, an unsupervised convolutional neural network algorithm, and a supervised convolutional neural network algorithm.

Software on one or more non-transitory information storage medium may configure the computer system 204 produce the segmented image 206 by additionally performing post-processing techniques on the segmented petrographic output image or reconstructed petrographic input image provided by the machine-learning algorithm(s). For example, simple linear iterative clustering (SLIC) can be performed on the segmented petrographic output image or reconstructed petrographic input image provided by the machine-learning algorithm to produce compact and highly uniform superpixels (cluster of pixels). A normalized graph cut technique can be performed on the superpixels to produce a finalized petrographic output image.

The computer system 204 can be configured to produce the segmented image 206 from the finalized petrographic output image, or to use the finalized petrographic output image as the segmented image 206; alternatively, the computer system 204 can be configured to produce the segmented image 206 from the segmented petrographic output image, or to use the segmented petrographic output image as the segmented image 206; alternatively, the computer system 204 can be configured to produce the segmented image 206 from the reconstructed petrographic input image, or to use the reconstructed petrographic input image as the segmented image 206.

The computer system 204 can be further configured to receive, send, produce, store, output, or a combination thereof, the segmented image 206. The computer system 204 can be further configured to determine a microfacies of the sample based on the segmented image 206 that is received, sent, produced, stored, output, or a combination thereof, by the computer system 204. The computer system 204 can be further configured to determine a microfacies characteristic of the sample based on the segmented image 206 that is received, sent, produced, stored, output, or a combination thereof, by the computer system 204.

In embodiments, the microfacies can be grainstone, packstone, wackestone, mudstone, rudstone, or the like. In embodiments, the microfacies characteristic can be any rock structural characteristic or any pore space characteristic. Examples of a rock structural characteristic include, but are not limited to, an abundance of allochems (rock grains or particles), grains and allochem grain types, inter-allochems mud-size material particles, the skeletal versus non-skeletal grains ratio, the compaction among grains, the cementation among grains, a grain type, a cement type, a grain radius distribution, a grain size distribution, a grain to inter-grains mud-size material (micrite mud matrix) ratio (an embodiment being an inter-grain micrite mud to grain ratio), a cement-to-grain ratio, or a combination thereof. Examples of pore space characteristics include, but are not limited to porosity (e.g., an inter-particle granular porosity, an intra-particle granular porosity, or a porosity value indicative of both) amount of dissolution pores such as vugs, a pore radius distribution, a pore size distribution, the connectivity of pores, amount of fractures, concentration of hydrocarbon, or a combination thereof. In some embodiments, the microfacies characteristic can be oil saturation.

In some embodiments, the machine-learning algorithm can be implemented on the computer system 204 for pore segmentation of the petrographic image 205. That is, performing the machine-learning algorithm on the petrographic image 205 by the computer system 204 can include performing the K-means clustering algorithm on the petrographic image 205 to segment pore regions from matrix regions in the petrographic image 205. In such embodiments, each pixel in the petrographic image 205 can be identified and assigned to a designated cluster. Designated clusters for pore segmentation can be a pore cluster and a matrix cluster. Groups of pixels in the pore cluster that are next to one another in the feature space defined by pixel intensity can be referred to pore regions of the petrographic image 205, and groups of pixels in the matrix cluster that are next to one another in the feature space defined by pixel intensity can be referred to as matrix regions of the petrographic image 205. The pixels identified and assigned into the porous cluster and the pixels identified and assigned into the matrix cluster collectively form the segmented petrographic output image for pore segmentation.

A distance transform and a watershed algorithm can be used on the segmented petrographic output image provided by the K-means clustering algorithm using the pore and matrix clusters as designated clusters to separate or divide the pore regions into individual pore spaces. Any distance transform and watershed algorithm can be used. A distance transform can provide the minima by computing the Euclidean distance from every pixel of the pore spaces to the background pixel. In some embodiments, the background pixel refers to a pixel in the matrix region (a matrix pixel). These minima are used as catchment basins for a watershed algorithm. In order to separate two connected pores, the watershed algorithm virtually "fills" the catchment basins with water until water from one of two connected pores touches the water from the other of the two connected pores. The contact line is used as a separating interface between the two connected pores. While flooding from the minima, the pixel connectivity is taken to be 8 as along with horizontal and vertical, the diagonal directions are also considered.

In some embodiments, a mask can be created for the pore spaces to segment the pore spaces from the rest of the pixels (e.g., the pixels in the matrix regions) in the segmented image 206. Using the segmented image 206, the computer system 204 can be configured to determine the porosity, pore radius distribution, pore size distribution, or a combination thereof of the sample. In some embodiments, pore segmentation by K-means clustering is performed on multiple petrographic images of the sample, and the computer system 204 can be configured to stack multiple segmented images (including segmented image 206) into a segmented three-dimensional image, and determine the porosity of the sample from the stack of multiple segmented images that form the segmented three-dimensional image.

In some embodiments, the machine-learning algorithm can be implemented by the computer system 204 for semantic segmentation of the petrographic image 205. Semantic segmentation is a deeper analysis of the petrographic image 205 than pore segmentation because more detail is segmented in semantic segmentation. In the disclosed method and system, semantic segmentation can include segmenting different grainstones in the petrographic image 205 from one another, segmenting pore spaces in the petrographic image 205 from matrix regions, segmenting cement from grainstones and from pore spaces in the petrographic image 205, and segmenting oil from the grainstones, pore spaces, and cement in the petrographic image 205, which can provide further insight into the geometric controls on the fluid flow. The grainstone structure can be significantly influenced by post-depositional diagenesis processes such as dissolution and recrystallization resulting in the presence of both intra-granular and inter-granular pore spaces and inter-granular cementation and crystal-growth on the surface layer and inside of some grains. Thus, segmentation of grains of rock from the cement that can exist between or among grains of the petrographic image 205 is important in understanding the microfacies characteristics of the sample and/or determining the microfacies of the rock(s) in the sample.

In some embodiments, performing the machine-learning algorithm can include performing the K-means clustering algorithm on the petrographic image 205 by the computer system 204 for semantic segmentation of the petrographic image 205. In semantic segmentation by K-means clustering, each pixel in the petrographic image 205 can be identified and assigned to a designated cluster. Designated clusters for semantic segmentation by K-means clustering can include a grain cluster, a cement cluster, a pore space cluster, and an oil cluster.

The computer system 204 can be configured to produce the segmented image 206 based on performing the K-means clustering algorithm, and the microfacies characteristic that is determined can be grain radius distribution, grain size distribution, oil saturation, cement-to-grain ratio, inter-grains micrite mud to grain ratio, or a combination thereof.

In some embodiments, performing the machine-learning algorithm can include processing the petrographic image 205 by the computer system 204 using one or more convolutional neural networks, for semantic segmentation of the petrographic image 205. In some embodiments, convolutional neural networks can have a U-net architecture or a W-net architecture. In semantic segmentation using one or more convolutional neural networks, each pixel in the petrographic image 205 can be identified and assigned to a designated category. Designated categories can include grain type (e.g., there are more than one grain type), cement type (e.g., there are more than one cement type), pore type (e.g., more than one size or type of pore space), and fluid type (e.g. there is more than one fluid type, for example, different hydrocarbon types).

In some particular embodiments, one or more convolutional neural networks having a U-net architecture can be utilized according to the present disclosure. The U-net architecture includes a down-sampling path and an up-sampling path with a total of 23 convolutional layers. Each step in the down-sampling path includes a repeated application of two 3×3 convolution layers, followed by rectified linear unit (RELU) for added non-linearity and batch normalization. Batch normalization helps prevent the slowing down of any training process for the convolutional neural network by handling the internal covariate shift that occurs when the normalizations for every mini-batch is lost during the training process. Each step (or convolution layer) is connected to the other by a 2×2 max pooling layer, and the number of channels are doubled so as to learn more features. The max pooling layer helps in reducing the dimension and parameters at each step. The final convolutional layer is connected to a 1×1 convolutional layer followed by a softmax layer that produced a K dimensional output where K corresponds to the number of categories for segmentation.

In other particular embodiments, one or more convolutional neural networks having a W-net architecture can be utilized according to the present disclosure. The W-net architecture contains two modules having configuration the same as or similar to the configuration of the U-net architecture, performed in series. The first U-net module of the W-net architecture receives the petrographic image 205 as the input and generates a segmentation map of the petrographic image 205, referred to herein as a segmented petrographic output image. The second U-net module of the W-net architecture receives the segmentation map generated by the first U-net module as the input and reconstructs the original input images, referred to herein as a reconstructed petrographic input image.

In embodiments, the resolution of the petrographic image, the resolution of the segmentation map, and the resolution of the reconstructed petrographic input image are the same.

In embodiments, differences between the petrographic image 205 and the reconstructed petrographic input image are considered loss. To minimize loss, the first U-net module can implement a soft normalized N cut loss function that determines loss between the segmentation map and the petrographic image 205, and the second U-net module can implement a reconstruction loss function that determines loss between the petrographic image 205 and the reconstructed petrographic input image. Both loss functions can be calibrated to minimize total loss so that the reconstructed petrographic input image learns the underlying representation of the petrographic image 205 with an acceptable degree of accuracy.

The computer system 204 can be configured to produce the segmented image 206 after performing the convolutional neural network algorithm, and the microfacies characteristic that is determined can be grain type, cement type, fluid type, grain radius distribution, grain size distribution, oil saturation, cement-to-grain ratio, inter-grains micrite mud to grain ratio, or a combination thereof.

In some embodiments, the convolutional neural network (s) can be trained with petrographic training data that includes image training data for multiple petrographic training images. The petrographic training images can have a training pixel resolution that is equal to an input pixel resolution of the petrographic image 205.

As discussed above, post-processing steps can be performed on the output of the machine-learning algorithm involving convolutional neural networks. In the context of convolutional neural network utilizing the W-net architecture, simple linear iterative clustering (SLIC algorithm) and normalized graph cut technique can be performed on the reconstructed petrographic input image provided by the W-net architecture to produce compact and highly uniform superpixels (after applying the SLIC algorithm) and a finalized petrographic output image (after applying normalized graphic cut technique on the superpixels). Performing SLIC on the reconstructed petrographic input image is useful when the machine-learning algorithm provides too much detail, such as in the case of W-net architecture. The SLIC algorithm can reduce the number of distance calculations as compared to K-means clustering because the search space for SLIC includes superpixels; whereas, the search space for K-means clustering is at the pixel level. Moreover, the superpixels produced by the SLIC algorithm are compact and highly uniform, which greatly reduces the computational complexity of subsequent image processing tasks. The normalized graph cut technique can increase the association between similar groups of pixels and decreases the dissociation between dissimilar groups of pixels. It has been found that implementing the combination of the SLIC algorithm and normalized graph cut technique after processing the petrographic image 205 in a machine-learning algorithm can recover the grain volume and grain boundaries to be consistent with the traditional definition of grains in petrographic image analysis.

In embodiments implementing convolutional neural networks having W-net architecture, it is contemplated that the segmented image 206 can be produced from the reconstructed petrographic input image provided by the convolutional neural networks without post-processing; alternatively, the segmented image 206 can be produced from the finalized petrographic output image provided by the normalized graph cut technique.

The microfacies analysis via machine-learning algorithms implemented on the computer system 204 is described above with reference to a single petrographic image 205; however, it is to be understood that the disclosed method and system contemplate microfacies analysis of a set (or a plurality) of petrographic images by the computer system 204. The bigger the set, the more advantageous the disclosed method and system become, since the benefit of implementing machine-learning on the computer system 204 to provide a microfacies analysis of petrographic images of samples increases with the number of images that are analyzed (e.g., analysis time savings, reduction in subjectivity across a large number of images etc.).

Figure 3:
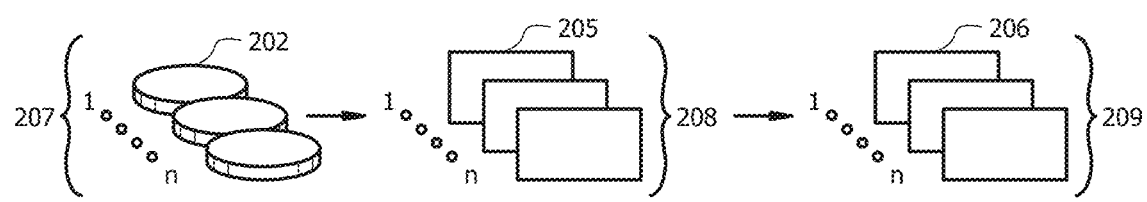
FIG. 3 is a perspective view schematically illustrating sets of thin sections, petrographic images, and segmented images.

FIG. 3 illustrates a set 207 of thin sections, a set 208 of petrographic images, and a set 209 of segmented images. Thin section 202 as discussed above can be among a set 207 of thin sections 1 to n that are cut from the core sample 201, and optionally from more than one sample of the subterranean formation 101. Similarly, petrographic image 205 as discussed above can be among a set 208 of petrographic images 1 to n. The set 208 can also be referred to as a stack of petrographic images 1 to n, which can approximate a three-dimensional petrographic image of at least a portion of the core sample 201. Segmented image 206 as discussed above can among a set 209 of segmented images 1 to n. The set 209 can also be referred to as a stack of segmented images 1 to n, which can approximate a segmented three-dimensional image of the three-dimensional petrographic image. The computer system 204 can be configured, according to any embodiment of the techniques described herein, i) to capture a set 208 of petrographic images 1 to n from a set 207 of thin sections 1 to n, and ii) to convert the set 208 of petrographic images 1 to n to a corresponding set 209 of segmented images 1 to n, where segmented image 1 corresponds to petrographic image 1, which corresponds to thin section 1, and so on, such that segmented image n corresponds to petrographic image n which corresponds to thin section n.

Figure 4:
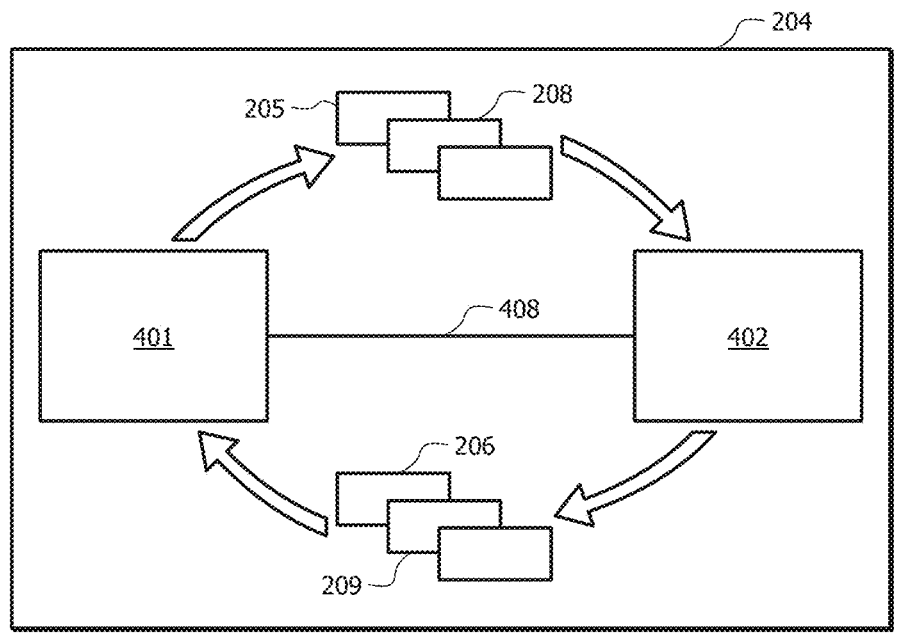
FIG. 4 is a schematic view of another embodiment of the disclosed computer system.

A particular embodiment of the computer system 204 is illustrated in FIG. 4. The computer system 204 in FIG. 4 has a first computer device 401 and a second computer device 402. By example only, the first computer device 401 can embodied as a desktop, laptop, smartphone, or tablet, and the second computer device 402 can be embodied as a big data platform. The first computer device 401 can be connected to the second computer device 402 via a communication link 403. The communication link 403 can include i) any wireless connection (e.g., Wi-Fi, Bluetooth) and/or a wired connection (e.g., Ethernet, USB) of the first computer device 401 on a LAN or WAN that is in turn networked with a VPN, cloud network, the Internet, or a combination thereof, and ii) any wireless connection (e.g., Wi-Fi, Bluetooth) and/or a wired connection (e.g., Ethernet, USB) of the second computer device 402 on a LAN or WAN that is in turn networked with a VPN, cloud network, the Internet, or a combination thereof.

In FIG. 4, the functions of the first computer device 401 include those described herein for converting a thin-slice 202 to a petrographic image 205 as described for FIG. 2, individually as applied to petrographic image 205 and as can be applied to each petrographic image 1 to n in petrographic image set 208. The first computer device 401 can be further configured to send the petrographic image 205 (individually or as part of a set 208 of petrographic images 1 to n) to the second computer device 402 and to receive segmented image 206 (individually or as part of a set 209 of segmented images 1 to n) from the second computer device 402. The functions of the second computer device 402 include those described herein for processing the petrographic image 205 with machine-learning algorithm(s) to generate a segmented image 206 as described for FIG. 2, individually as applied to petrographic image 205 and as can be applied to each petrographic image 1 to n in petrographic image set 208. The second computer device 402 can be further configured to receive the petrographic image 205 (individually or as part of a set 208 of petrographic images 1 to n) from the first computer device 401 and to send segmented image 206 (individually or as part of a set 209 of segmented images 1 to n) to the first computer device 401.

In embodiments where the second computer device 402 is a third-party big data platform such as MICROSOFT AZURE, SAP CLOUD PLATFORM, and ORACLE CLOUD INFRASTRUCTURE, the first computer device 401 can send (e.g., upload) petrographic image 205, and optionally a set 208 of petrographic images 1 to n, to the big data platform via an Internet connection for processing of the petrographic images 205 by the big data platform to produce the segmented image 206, and optionally a set 209 of segmented images 1 to n. The first computer device 401 can be configured to receive the segmented image 206, optionally the set 209 of segmented images 1 to n from the second computer device 402, via the Internet connection.

After determining a microfacies or a microfacies characteristic, the present method and system contemplate further action can be taken based on the microfacies characteristics.

In some embodiments, the method can further include drilling, completing, or producing hydrocarbons from a wellbore formed in the subterranean formation based on the microfacies characteristic of the sample that is determined based on the segmented image 206. Any drilling, completion, and production technique can be implemented within the scope of this disclosure.

Figure 5:
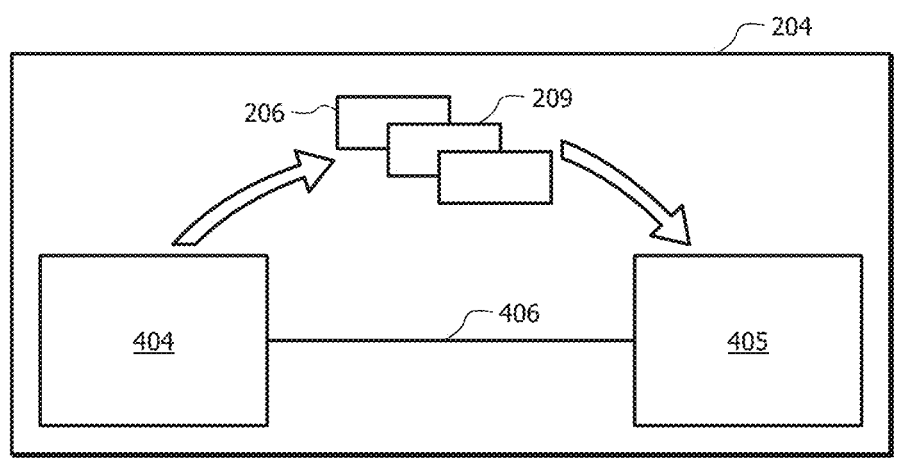
FIG. 5 is a schematic view of another embodiment of the disclosed computer system.

In some embodiments, the microfacies and/or microfacies characteristic obtained by the disclosed system and method can be used for reservoir modeling. FIG. 5 illustrates another embodiment of the computer system 204 that can include a first computer device 404 and a second computer device 405. By example only, each of the first computer device 404 and the second computer device 405 can embodied as a desktop, laptop, smartphone, or tablet. The first computer device 404 can be connected to the second computer device 405 via a communication link 406. The communication link 406 can include i) any wireless connection (e.g., Wi-Fi, Bluetooth) and/or a wired connection (e.g., Ethernet, USB) of the first computer device 404 on a LAN or WAN that is in turn networked with a VPN, cloud network, the Internet, or a combination thereof, and ii) any wireless connection (e.g., Wi-Fi, Bluetooth) and/or a wired connection (e.g., Ethernet, USB) of the second computer device 405 on a LAN or WAN that is in turn networked with a VPN, cloud network, the Internet, or a combination thereof.

In FIG. 5, the functions of the first computer device 404 include those described herein for converting a thin-slice 202 to a petrographic image 205 as described for FIG. 2, individually as applied to petrographic image 205 and as can be applied to each petrographic image 1 to n in petrographic image set 208. The functions of the first computer device 404 can also include the processing of the petrographic image(s) as described herein; alternatively, a separate computer device (e.g., second computer device 402 of FIG. 4) can be used for the processing. The functions of the second computer device 405 in FIG. 5 include those of a reservoir modeling computer. The functions of the second computer device 405 can include receiving the microfacies and/or microfacies characteristic of the core sample 201 that is determined based on the segmented image 206; and modeling features of at least a portion of the subterranean formation 101 using the microfacies and/or microfacies characteristic. The reservoir modeling computer can be configured to receive and model features of at least a portion of the subterranean formation 101 using a set 209 of segmented images 1 to n (from FIG. 3).

EXAMPLES

The following examples are illustrative of the embodiments of the method and system disclosed herein.

Examples 1 to 3 below automate microfacies analysis of petrographic images 601, 801, and 1001 according to embodiments of the disclosed method and system. The petrographic images 601, 801, and 1001 used in each of Examples 1 to 3 include a slightly packed ooidal-dominated grainstone with isolated calcite cements and scattered residual oil. The ooidal-dominated grainstone is one type of grainstone found in carbonate rock. Other types of grainstone which can be analyzed in the method and by the system include bioclastic-dominated (skeletal) grainstone, peloidal-dominated grainstone, and intraclastic-dominated grainstone. While the examples analyze an ooidal-dominated grainstone and thus a carbonate rock, it is contemplated that the method and system disclosed herein can be utilized for different types of rock found in a subterranean formation. Due to the heterogeneous structure of the grainstones of carbonate rock, it is very difficult to manually label or interpret its facies characteristics, and the disclosed method and system provide easy analysis via automation.

Example 1

Example 1 demonstrates the use of an unsupervised K-means clustering algorithm as the machine-learning algorithm for pore segmentation of a petrographic image 601. The petrographic image 601 has a resolution of 1400 pixels by 900 pixels. The petrographic image 601 contains grains 610, pore space 611 between grains (for ooidal-dominated grainstones) 610, cement (calcite) 612, and oil 613. Because the space 611 between the grains 610 of the petrographic image 601 has a distinct color due to the dye used in the thin section, pixel intensities (as defined by the red, green, and blue intensity per pixel) were used as the threshold for determining whether a pixel was assigned to the pore cluster or to the matrix cluster.

Figure 6:
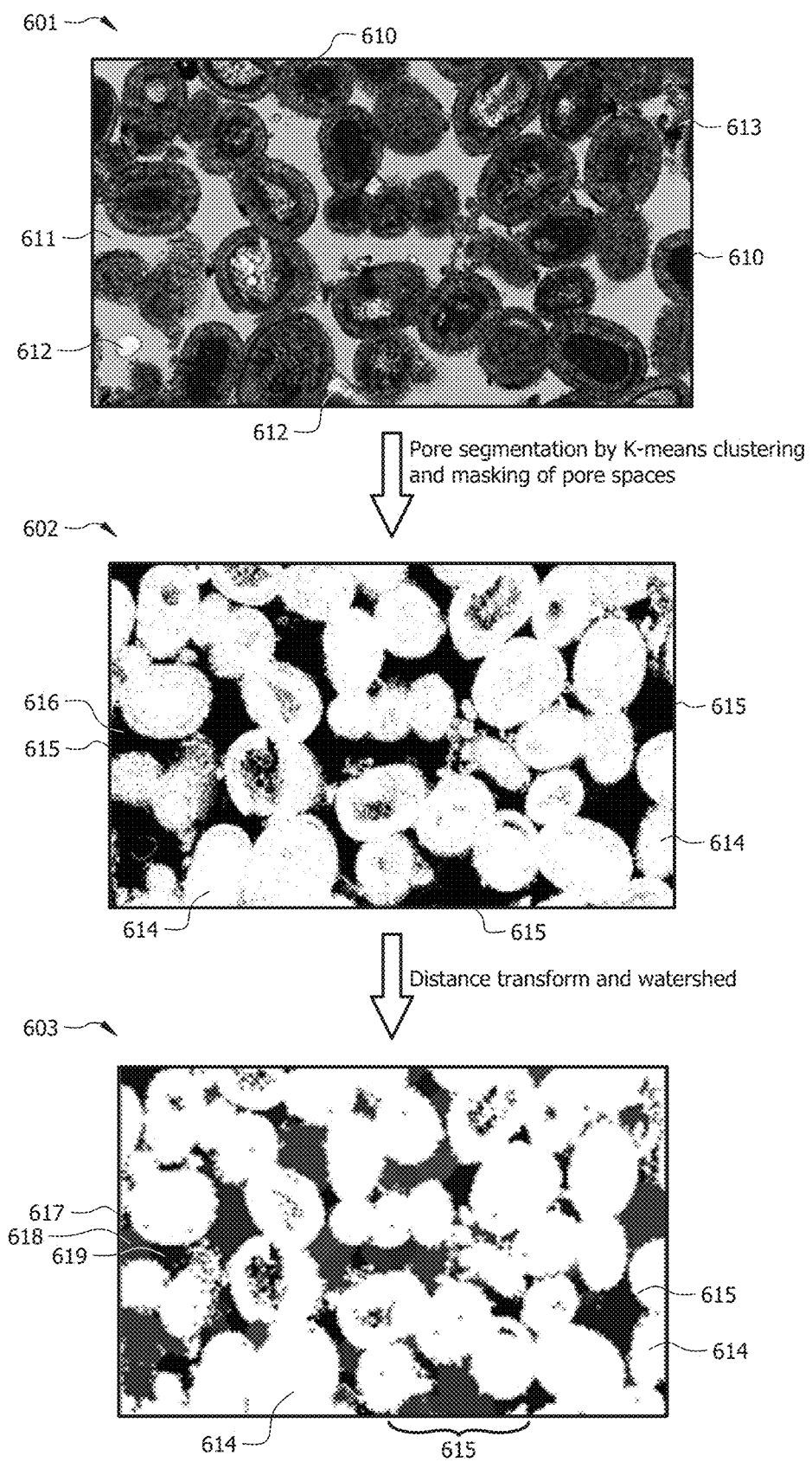
FIG. 6 is a series of plan views of a petrographic image, a segmented petrographic output image, and a finalized petrographic output image, where the segmented petrographic output image is segmented into two designated clusters (pore cluster and matrix cluster) by performing an unsupervised K-means clustering algorithm on the petrographic image, and the finalized petrographic output image is produced after performing a distance transform and watershed algorithm on the segmented petrographic output image.

FIG. 6 illustrates plan views of the segmented petrographic output image 602 produced when performing pore segmentation by K-means clustering with two designated clusters (pore cluster and matrix cluster) on petrographic image 601, and the finalized petrographic output image 603 produced after performing a distance transform and watershed algorithm on the segmented petrographic output image 602. The pixels of the petrographic image 601 were identified as assigned into the pore cluster (e.g., indicated in FIG. 6 by pore regions 615) and the matrix cluster (e.g., indicated in FIG. 6 by matrix regions 614). The K-means clustering algorithm assigned oil pixels and water/dye pixels to the porous region 615.

A mask (black appearance in the image 602) was created for the pore regions 615 in the segmented petrographic output image 602 to amplify the segmentation of the pore regions 615 (e.g., containing space 611 between grains 610) from the matrix regions 614 (e.g., containing the grains 610).

After pore segmentation of the petrographic image 601 by K-means clustering, it was determined, using the segmented petrographic output image 602, that the pore regions 615 occupy about 23.4% of the segmented petrographic output image 602. For comparison, the routine core analysis (RCA) based porosity of the core plug was determined to be 21.2%, so the determined pore region percentage is close to the actual porosity.

After performing a distance transform and watershed algorithm on the segmented petrographic output image 602, the finalized petrographic output image 603 was produced. The finalized petrographic output image 603 includes the pore regions 615 divided into individual pore spaces. For example, pore region 616 of the segmented petrographic output image 602 is divided into pore spaces 617, 618, and 619 in the finalized petrographic output image 603.

Figure 7A:
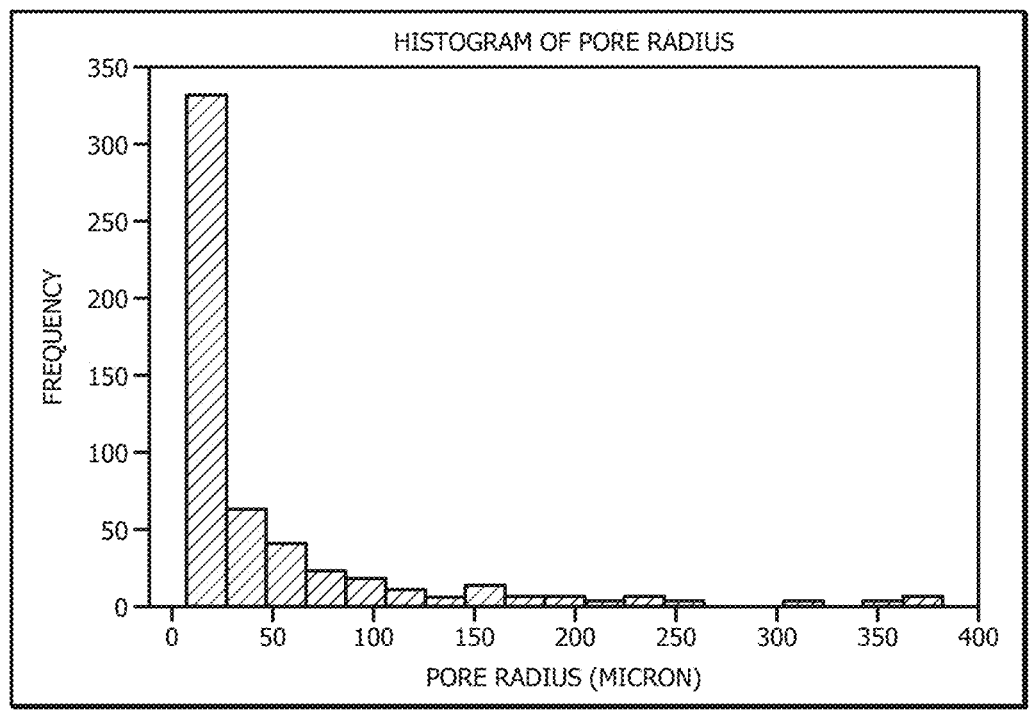
FIG. 7A is a graph of the frequency versus pore radius in the finalized petrographic output image in FIG. 6.
Figure 7B:
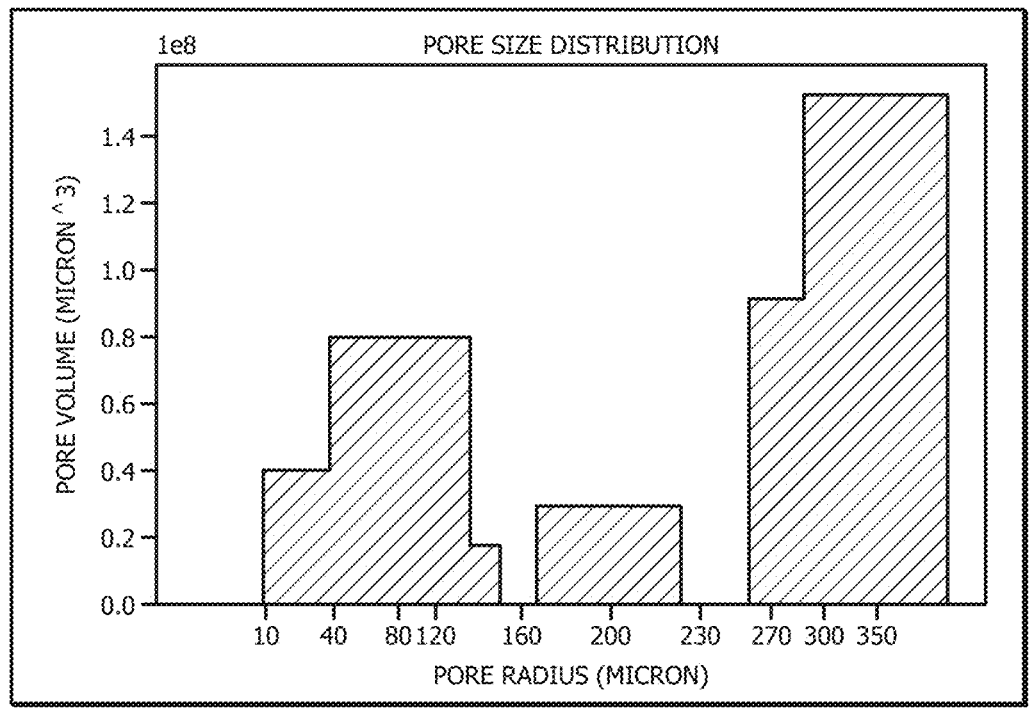
FIG. 7B is a graph of pore volume versus pore radius in the finalized petrographic output image in FIG. 6.

From the finalized petrographic output image 603, the pore radius and the pore size distribution were determined. A graph of the frequency versus pore radius in the finalized petrographic output image 603 is shown in FIG. 7A, and a graph of pore volume versus pore radius in the finalized petrographic output image 603 is shown in FIG. 7B. Pore volume was estimated by assuming the thickness was the same for all pore spaces.

Example 2

Example 2 demonstrates the use of an unsupervised K-means clustering algorithm as the machine-learning algorithm for semantic segmentation of a petrographic image 801. The petrographic image 801 has a resolution of 1400 pixels by 900 pixels. The thickness of the thin section that was used in capturing the petrographic image 801 was between 30 to 50 microns. The petrographic image 801 contains grains 810, intergranular pore space 811 between grains (for ooidal-dominated grainstones) 810, cement (calcite) 812, and oil 813.

Figure 8:
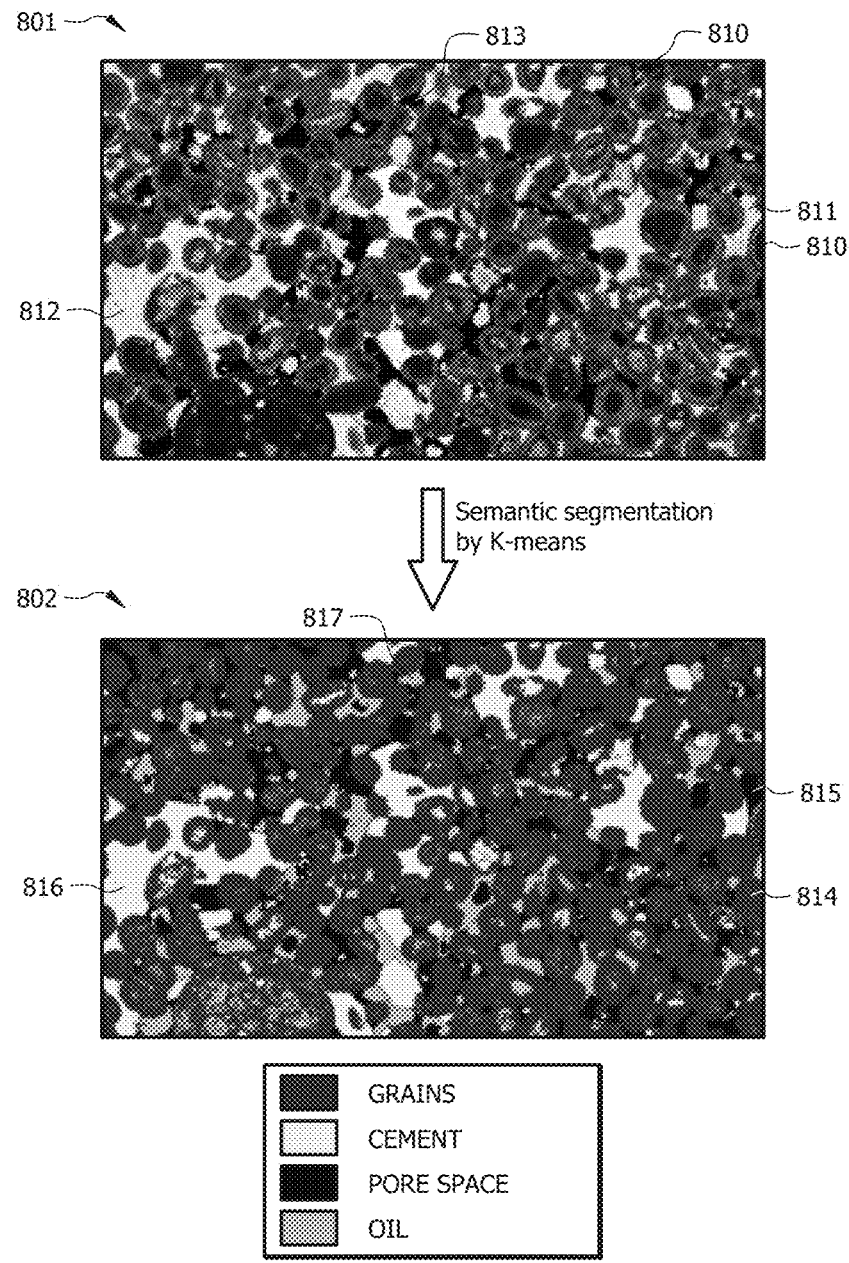
FIG. 8 is a series of plan views of a petrographic image and a segmented petrographic output image, where the petrographic image is segmented into four designated clusters (grain cluster, cement cluster, pore space cluster, and oil cluster) by performing an unsupervised K-means clustering on the petrographic image.

FIG. 8 illustrates the segmented petrographic output image 802 produced after performance of semantic segmentation by K-means clustering with four designated clusters (grain cluster, cement cluster, pore space cluster, and oil cluster) on the petrographic image 801. The cement cluster also includes any micrite matrix. The segmented petrographic output image 802 has each pixel identified and assigned to the grain cluster 814, the pore space cluster 815, the cement cluster 816, or the oil cluster 817. Pixel intensities (as defined by the red, green, and blue intensity per pixel) were used as the threshold for determining which cluster a pixel was assigned.

After semantic segmentation of the petrographic image 801 by K-means clustering, it was determined, using the segmented petrographic output image 802, that oil saturation was 40% and the cement-to-grain ratio was 17%.

Figure 9A:
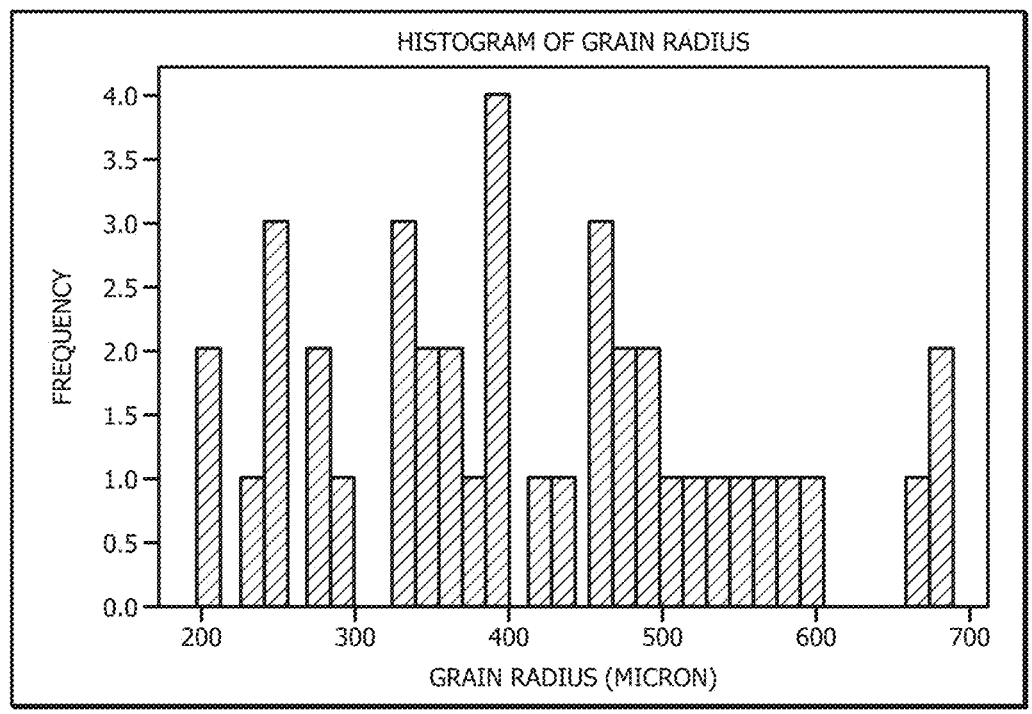
FIG. 9A is a graph of the frequency versus grain radius in the segmented petrographic output image of FIG. 8.
Figure 9B:
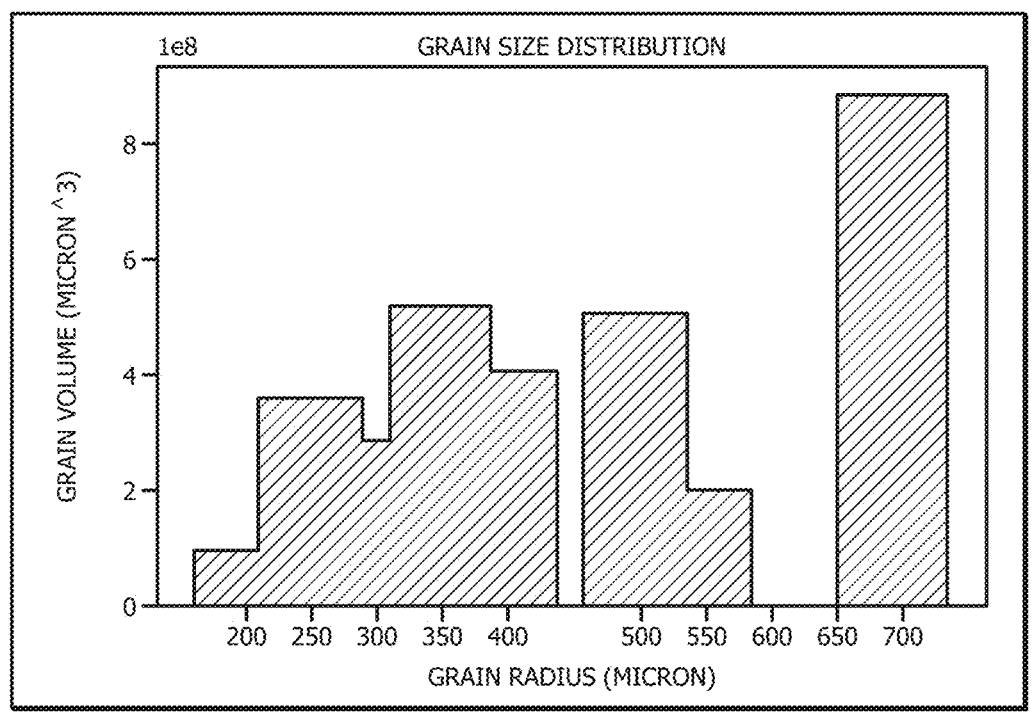
FIG. 9B is a graph of grain volume versus grain radius in the segmented petrographic output image of FIG. 8.

Also, the grain radius and the grain size distribution were determined from the segmented petrographic output image 802. A graph the frequency versus grain radius in the segmented petrographic output image 802 is shown in FIG. 9A, and a graph of grain volume versus grain radius in the segmented petrographic output image 802 is shown in FIG. 9B. Grain volume was estimated by assuming the thickness was the same for all grains.

Example 3

Example 3 demonstrates the use of an unsupervised machine-learning algorithm by convolutional neural network having W-net architecture for semantic segmentation of a petrographic image 1001. The convolutional neural network takes into account pixel intensity, textural information (e.g., color gradients) and many other features. There is no clustering involved in convolutional neural networks. Instead, the convolutional neural networks convolve the petrographic image 1001 with a number of filters, each convolution with a filter will transform the image 1001 into a new two-dimensional matrix, also called a feature map. These feature maps with various filters are the feature set for convolutional neural networks. These feature maps capture more features of the petrographic image 1001 than a clustering algorithm.

The petrographic image 1001 has a resolution of 128 pixels by 128 pixels and is a 128 pixel by 128 pixel portion of the petrographic image 801 used in Example 2. The petrographic image 1001 contains grains (for ooidal-dominated grainstones) 1010, space 1011 between grains 1010, and oil 1013. While petrographic image 1001 does not contain cement, it is contemplated that any cement would be identified and assigned to the corresponding category by the convolutional neural networks.

Before processing the petrographic image 1001 in the W-net unsupervised convolutional neural network, image training data for training the W-net unsupervised convolutional neural network was prepared. Particularly, petrographic training images made by cropping, rotating, adding noise, and varying light intensity of the 24 petrographic images (resolution of 1400 pixels by 900 pixels) were collectively used as the image training data. In order to make training faster, the petrographic training images in the image training data were resized to 128 pixels by 128 pixels. A batch size of 5 petrographic training images with an initial learning rate of $10^{-5}$ for a total of 40,000 iterations was used for training from scratch. The learning rate was then subsequently halved after every 10,000 iterations.

Figure 10:
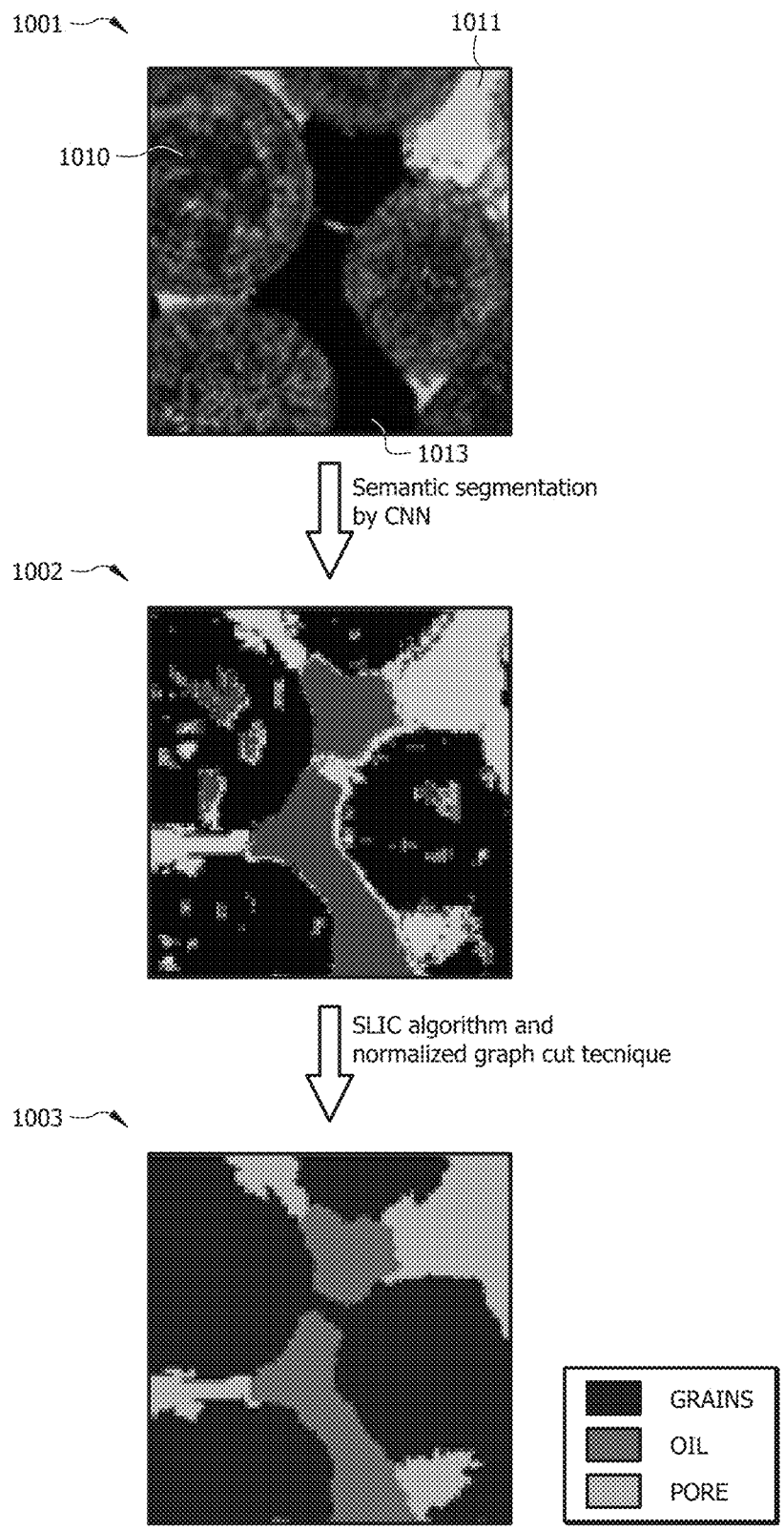
FIG. 10 is a series of plan views of a petrographic image, a reconstructed petrographic input image, and a finalized petrographic output image, where the reconstructed petrographic input image is produced by performing an unsupervised machine-learning algorithm based on deep convolutional neural networks having a W-net architecture on the petrographic image, and the finalized petrographic output image is produced by performing a SLIC algorithm and a normalized graph cut technique on the reconstructed petrographic input image.
Figure 11:
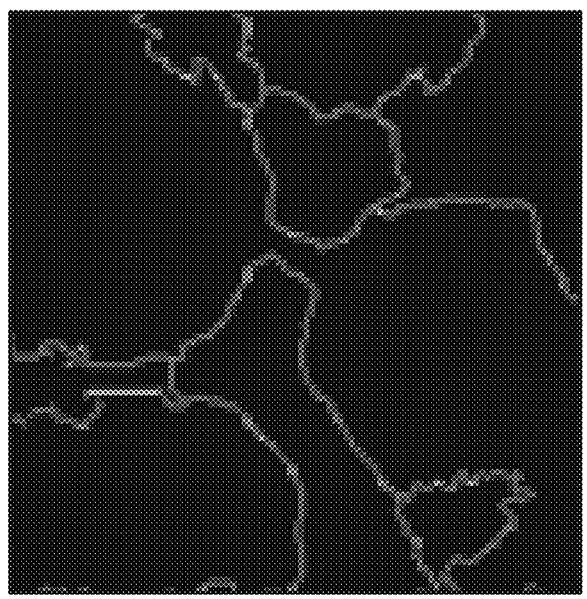
FIG. 11 is a plan view of an edge detection image derived from the petrographic image, for comparison with the images in FIG. 10.

The petrographic image 1001 having an input pixel resolution of 128 pixels by 128 pixel (which was chosen so as to match the training pixel resolution of 128 pixels by 128 pixels) was then processed in the W-net unsupervised convolutional neural network. The reconstructed petrographic input image 1002 was produced, and is shown in FIG. 10. The reconstructed petrographic input image 1002 is over-segmented, so it was found that post-processing using a SLIC algorithm and then a normalized graph cut technique compensated for the over-segmentation of the W-net unsupervised convolutional neural network. The finalized petrographic output image 1003 after using these post-processing steps is shown in FIG. 10.

An edge detection image 1101 was obtained by marking the boundaries around the regions where different regions are marked by different integer values in the finalized petrographic output image 1003. A comparison of the edge detection image 1101 of the petrographic image 1001 with the cluster boundaries in the finalized petrographic output image 1003 shows that adding these post-processing steps recovers the grain volume and grain boundaries from the over-segmented image 1002 to be consistent with the traditional definition of grains. Thus, it appears that post-processing when processing petrographic images in a W-net unsupervised convolutional neural network improves microfacies analysis by recovering grain volume and grain boundaries.

Additional Disclosure

The following are non-limiting, specific embodiments in accordance with the present disclosure:

Embodiment 1A. A method for analysis of a petrographic image of a sample of a subterranean formation, the method comprising: performing a machine-learning algorithm on the petrographic image; and determining a microfacies or a microfacies characteristic of the sample based on a segmented image provided by the machine-learning algorithm that is performed on the petrographic image.

Embodiment 1B. The method of 1A, wherein the machine-learning algorithm is supervised or unsupervised.

Embodiment 1C. The method of 1A or 1B, wherein the microfacies characteristic is selected from an abundance of allochems (rock grains or particles), grains and allochem grain types, inter-allochems mud-size material particles, the skeletal versus non-skeletal grains ratio, the compaction among grains, the cementation among grains, a grain type, a cement type, a grain radius distribution, a grain size distribution, a grain to inter-grains mud-size material ratio, a cement-to-grain ratio, porosity (e.g., an inter-particle granular porosity, an intra-particle granular porosity, or a porosity value indicative of both), amount of dissolution pores such as vugs, a pore radius distribution, a pore size distribution, the connectivity of pores, amount of fractures, concentration of hydrocarbon, oil saturation, or a combination thereof.

Embodiment 1D. The method of any of 1A to 1C, wherein performing an unsupervised machine-learning algorithm on the petrographic image comprises: performing a K-means clustering algorithm on the petrographic image to produce a segmented petrographic output image having pore regions segmented from matrix regions; utilizing a distance transform and a watershed algorithm on the segmented petrographic output image to produce a finalized petrographic output image having the pore regions segmented to into individual pore spaces; producing the segmented image having the pore regions segmented into individual pore spaces and the pore regions segmented from the matrix regions;

Embodiment 1E. The method of 1D, wherein the microfacies characteristic of the sample that is determined is porosity, pore radius distribution, pore size distribution, or a combination thereof.

Embodiment 1F. The method of any of 1A to 1E, wherein performing a machine-learning algorithm on the petrographic image comprises or further comprises: performing a K-means clustering algorithm on the petrographic image to identify each pixel in the petrographic image as being part of a grain cluster, a cement cluster, a pore space cluster, or an oil cluster; and producing the segmented image based on performing the K-means clustering algorithm.

Embodiment 1G. The method of 1F, wherein the microfacies characteristic of the sample that is determined is grain radius distribution, grain size distribution, oil saturation, cement-to-grain ratio, or a combination thereof.

Embodiment 1H. The method of 1 A to 1G, wherein performing a machine-learning algorithm on the petrographic image comprises or further comprises: processing the petrographic image by a convolutional neural network to identify each pixel in the petrographic image as a grain type, cement type, a pore space, or oil; and producing the segmented image after processing.

Embodiment 1I. The method of 1H, wherein the microfacies characteristic of the sample that is determined is grain type, cement type, fluid type, grain radius distribution, grain size distribution, oil saturation, cement-to-grain ratio, inter-grains micrite mud to grain ratio, or a combination thereof.

Embodiment 1J. The method of 1H or 1I, wherein the convolutional neural network has a U-net architecture or a W-net architecture.

Embodiment 1K. The method of any of 1A to 1J, wherein performing a machine-learning algorithm on the petrographic image further comprises: performing simple linear iterative clustering on a reconstructed petrographic input image provided by the convolutional neural network to produce compact and highly uniform superpixels; and performing a normalized graph cut technique on the superpixels to produce a finalized petrographic output image.

Embodiment 1L. The method of 1K, wherein the segmented image is produced from the finalized petrographic output image.

Embodiment 1M. The method of any of 1H to 1L, wherein performing a machine-learning algorithm on the petrographic image further comprises training the convolutional neural network with petrographic training data, wherein the petrographic training data comprises image training data for a plurality of petrographic training images.

Embodiment 1N. The method of 1M, wherein each of the plurality of petrographic training images has a training pixel resolution, wherein an input pixel resolution of the petrographic image is equal to the training pixel resolution.

Embodiment 1O. The method of any of 1A to 1N, further comprising: capturing, by an image capture device, the petrographic image of the sample of the subterranean formation.

Embodiment 1P. The method of any of 1A to 1O, further comprising: drilling, completing, or producing hydrocarbons from a wellbore formed in the subterranean formation based on the microfacies characteristic of the sample that is determined based on the segmented image.

Embodiment 1Q. The method of any of 1A to 1P, further comprising: receiving, by a reservoir modeling computer, the microfacies characteristic of the sample that is determined based on the unsupervised machine-learning algorithm that is performed on the petrographic image; and modeling, by the reservoir modeling computer, features of at least a portion of the subterranean formation using the microfacies characteristic.

Embodiment 2A. A method for analysis of a petrographic image of a sample of a subterranean formation, the method comprising determining a microfacies characteristic of the sample based on a segmented image of the petrographic image, wherein the segmented image is derived from the petrographic image using a machine-learning algorithm.

Embodiment 2B, which is the method of 2A, wherein the microfacies characteristic is selected from an abundance of allochems (rock grains or particles), grains and allochem grain types, inter-allochems mud-size material particles, the skeletal versus non-skeletal grains ratio, the compaction among grains, the cementation among grains, a grain type, a cement type, a grain radius distribution, a grain size distribution, a grain to inter-grains mud-size material ratio, a cement-to-grain ratio, porosity (e.g., an inter-particle granular porosity, an intra-particle granular porosity, or a porosity value indicative of both), amount of dissolution pores such as vugs, a pore radius distribution, a pore size distribution, the connectivity of pores, amount of fractures, concentration of hydrocarbon, oil saturation, or a combination thereof.

Embodiment 2C, which is the method of 2A or 2B, wherein the machine-learning algorithm is supervised or unsupervised.

Embodiment 2D, which is the method of any of 2A to 2C, wherein the machine-learning algorithm is or comprises a K-means clustering algorithm.

Embodiment 2E, which is the method of 2D, further comprising: performing the K-means clustering algorithm on the petrographic image to segment pore regions from matrix regions in the petrographic image; utilizing a distance transform and a watershed algorithm to separate the segmented pore regions to into individual pore spaces; producing the segmented image having the pore spaces segmented from the matrix regions; wherein the microfacies characteristic of the sample that is determined is porosity, pore radius distribution, pore size distribution, or a combination thereof.

Embodiment 2F, which is the method of 2D or 2E, further comprising: performing the K-means clustering algorithm on the petrographic image to identify each pixel in the petrographic image as being part of a grain cluster, a cement cluster, a pore space cluster, or an oil cluster; producing the segmented image based on performing the K-means clustering algorithm; wherein the microfacies characteristic of the sample that is determined is grain radius distribution, grain size distribution, oil saturation, cement-to-grain ratio, or a combination thereof.

Embodiment 2G, which is the method of any of 2A to 2F, wherein the machine-learning algorithm is or further comprises a convolutional neural network.

Embodiment 2H, which is the method of 2G, further comprising: using a convolutional neural network on the petrographic image to identify each pixel in the petrographic image to be a grain type, cement type, pore space, or a fluid type (e.g., oil); and producing the segmented image; wherein the microfacies characteristic of the sample that is determined is grain type, cement type, fluid type, grain radius distribution, grain size distribution, oil saturation, cement-to-grain ratio, inter-grains micrite mud to grain ratio, or a combination thereof.

Embodiment 2I, which is the method of 2G or 2H, wherein the convolutional neural network has a U-net architecture or a W-net architecture.

Embodiment 2J, which is the method of any of 2A to 2I, further comprising post-processing of a reconstructed petrographic input image produced by the machine-learning algorithm.

Embodiment 2K, which is the method of 2J, wherein post-processing comprises: performing simple linear iterative clustering (SLIC algorithm) on the reconstructed petrographic input image provided by the convolutional neural network to produce superpixels (e.g., compact and highly uniform superpixels that greatly reduce the computational complexity of subsequent image processing tasks).

Embodiment 2L, which is the method of 2K, wherein post-processing further comprises: performing a normalized graph cut technique on the superpixels to produce a finalized petrographic output image.

Embodiment 2M, which is the method of 2L, wherein the segmented image is produced from the finalized petrographic output image; or further comprising producing the segmented image from the finalized petrographic output image.

Embodiment 2N, which is the method of any of 2A to 2M, further comprising: training the machine-learning algorithm.

Embodiment 2O, which is the method of 2N, wherein training comprising: training the convolutional neural network model using petrographic training data, wherein the petrographic training data comprises image training data for a plurality of petrographic training images.

Embodiment 2P, which is the method of 2O, wherein each of the plurality of petrographic training images has a training pixel resolution, wherein an input pixel resolution of the petrographic image is equal to the training pixel resolution.

Embodiment 2Q, which is the method of any of 2A to 2P, further comprising capturing, by an image capture device, the petrographic image of the sample of the subterranean formation.

Embodiment 2R, which is the method of any of 2A to 2Q, further comprising: drilling, completing, or producing hydrocarbons from a wellbore formed in the subterranean formation based on the microfacies characteristic of the sample that is determined based on the segmented image.

Embodiment 2S, which is the method of any of 2A to 2R, further comprising: receiving, by a reservoir modeling computer, the microfacies characteristic of the sample that is determined based on the unsupervised machine-learning algorithm that is performed on the petrographic image; and modeling, by the reservoir modeling computer, features of at least a portion of the subterranean formation using the microfacies characteristic.

Embodiment 3A. A method for analysis of a petrographic image of a sample of a subterranean formation, the method comprising:
determining a first microfacies characteristic of the sample based on a first segmented image of the petrographic image, wherein the first segmented image is derived by performing pore segmentation on the petrographic image with a K-means clustering algorithm;
determining a second microfacies characteristic of the sample based on a second segmented image of the petrographic image, wherein the second segmented image is derived by performing semantic segmentation on the petrographic image with a K-means clustering algorithm; and
determining third microfacies characteristic of the sample based on third segmented images of the petrographic images, wherein the third segmented images are derived by performing semantic segmentation on the petrographic images by a convolutional neural network.

Embodiment 3B. The method of 3A, wherein the first microfacies characteristic includes a pore radius, a pore size distribution, or both; wherein the second microfacies characteristic includes a grain radius, a grain size distribution, or both; wherein the third microfacies characteristic includes a grain type, a cement type, a fluid type, an oil saturation, a cement-to-grain ratio, or a combination thereof.

Embodiment 3C. The method of 3A or 3B, wherein the K-means clustering algorithm in the pore segmentation is unsupervised, wherein the K-means clustering algorithm for the semantic segmentation is unsupervised, wherein the convolutional neural network algorithm for the semantic segmentation is unsupervised, or a combination thereof.

Embodiment 3D. The method of any of 3A to 3C, further comprising: training the convolutional neural network according to a technique disclosed herein.

Embodiment 3E. The method of any of 3A to 3D, further comprising: post-processing a reconstructed petrographic input image provided by the convolutional neural network to produce a final segmented image.

Embodiment 3F. The method of 3E, wherein post-processing comprises performing a SLIC algorithm and normalized graphic cut technique on the reconstructed petrographic input image to produce the final segmented image.

Embodiment 4A. A computer system for analysis of a petrographic image of a sample of a subterranean formation, comprising: a computer device having at least one memory and at least one processor, wherein the at least one memory and the at least one processor are respectively configured to store and execute instructions for causing the computer device to: perform a machine-learning algorithm on the petrographic image; and determine a microfacies or a microfacies characteristic of the sample based on a segmented image provided by the machine-learning algorithm.

Embodiment 4B. The computer system of 4A, wherein the machine-learning algorithm is supervised or unsupervised.

Embodiment 4C. The computer system of 4A or 4B, wherein the machine-learning algorithm is or comprises an unsupervised K-means clustering algorithm.

Embodiment 4D. The computer system of any of 4A to 4C, wherein the machine-learning algorithm is unsupervised and is performed by a convolutional neural network having a U-net architecture or a W-net architecture.

Embodiment 4E. The computer system of any of 4A to 4D, wherein the microfacies characteristic is selected from an abundance of allochems (rock grains or particles), grains and allochem grain types, inter-allochems mud-size material particles, the skeletal versus non-skeletal grains ratio, the compaction among grains, the cementation among grains, a grain type, a cement type, a grain radius distribution, a grain size distribution, a grain to inter-grains mud-size material ratio, a cement-to-grain ratio, porosity (e.g., an inter-particle granular porosity, an intra-particle granular porosity, or a porosity value indicative of both), amount of dissolution pores such as vugs, a pore radius distribution, a pore size distribution, the connectivity of pores, amount of fractures, concentration of hydrocarbon, oil saturation, or a combination thereof.

Embodiment 4F. The computer system of any of 4A to 4E, further comprising: an image capture device coupled to the computer device, wherein the image capture device is configured to capture the petrographic image of the sample of the subterranean formation; and wherein the instructions cause the computer device to: receive the petrographic image from the image capture device.

Embodiment 4G. The computer system of any of 4A to 4F, further comprising: a reservoir modeling computer coupled to the computer device and having at least one memory and at least one processor, wherein the at least one memory of the reservoir modeling computer and the at least one processor of the reservoir modeling computer are respectively configured to store and execute instructions for causing the reservoir modeling computer to: receive, from the computer device, the microfacies characteristic of the sample that is determined based on the segmented image provided by the unsupervised machine-learning algorithm; and model features of at least a portion of the subterranean formation using the microfacies characteristic.

Embodiment 4H. The computer system of any of 4A to 4G, wherein the computer device includes a big data platform.

Embodiment 4I. The computer system of any of 4A to 4H, wherein the instructions cause the computer device to: perform simple linear iterative clustering on a reconstructed petrographic input image provided by the machine-learning algorithm to produce compact and highly uniform superpixels; and perform a normalized graph cut technique on the superpixels to produce a finalized petrographic output image, wherein the finalized petrographic output image is used as the segmented image.

Embodiment 5A. A computer system for analysis of a petrographic image of a sample of a subterranean formation, comprising: a computer device having at least one memory and at least one processor, wherein the at least one memory and the at least one processor are respectively configured to store and execute instructions for causing the computer device to: determine a microfacies or a microfacies characteristic of the sample based on a segmented image of the petrographic image, wherein the segmented image is derived from the petrographic image using a machine-learning algorithm.

Embodiment 5B. The computer system of 5A, wherein the computer device is configured to receive the segmented image from a second computer device, the second computer device having at least one memory and at least one processor, wherein the at least one memory and the at least one processor are respectively configured to store and execute instructions for causing the second computer device to perform the machine-learning algorithm on the petrographic image to produce the segmented image.

Embodiment 5C. The computer system of 5A or 5B, wherein the machine-learning algorithm is supervised or unsupervised.

Embodiment 5D. The computer system of any of 5A to 5C, wherein the machine-learning algorithm is or comprises an unsupervised K-means clustering algorithm.

Embodiment 5E. The computer system of any of 5A to 5D, wherein the machine-learning algorithm is unsupervised and is performed by a convolutional neural network having a U-net architecture or a W-net architecture.

Embodiment 5F. The computer system of any of 5B to 5E, wherein the instructions cause the second computer device to: perform simple linear iterative clustering on a reconstructed petrographic input image provided by the machine-learning algorithm to produce compact and highly uniform superpixels; and perform a normalized graph cut technique on the superpixels to produce a finalized petrographic output image, wherein the finalized petrographic output image is used as the segmented image.

Embodiment 5G. The computer system of any of 5A to 5F, wherein the microfacies characteristic is selected from an abundance of allochems (rock grains or particles), grains and allochem grain types, inter-allochems mud-size material particles, the skeletal versus non-skeletal grains ratio, the compaction among grains, the cementation among grains, a grain type, a cement type, a grain radius distribution, a grain size distribution, a grain to inter-grains mud-size material ratio, a cement-to-grain ratio, porosity (e.g., an inter-particle granular porosity, an intra-particle granular porosity, or a porosity value indicative of both), amount of dissolution pores such as vugs, a pore radius distribution, a pore size distribution, the connectivity of pores, amount of fractures, concentration of hydrocarbon, oil saturation, or a combination thereof.

Embodiment 5H. The computer system of any of 5A to 5G, further comprising: an image capture device coupled to the computer device, wherein the image capture device is configured to capture the petrographic image of the sample of the subterranean formation; and wherein the instructions cause the computer device to: receive the petrographic image from the image capture device.

Embodiment 5I. The computer system of any of 5A to 5H, further comprising: a reservoir modeling computer coupled to the computer device and having at least one memory and at least one processor, wherein the at least one memory of the reservoir modeling computer and the at least one processor of the reservoir modeling computer are respectively configured to store and execute instructions for causing the reservoir modeling computer to: receive, from the computer device, the microfacies characteristic of the sample that is determined based on the segmented image provided by the unsupervised machine-learning algorithm; and model features of at least a portion of the subterranean formation using the microfacies characteristic.

Embodiment 6A. A computer system for analysis of a petrographic image of a sample of a subterranean formation, comprising: one or more computer devices, each computer device having at least one memory and at least one processor, wherein the at least one memory and the at least one processor are respectively configured to store and execute instructions for causing the one or more computer devices to:

determine a first microfacies characteristic of the sample based on a first segmented image of the petrographic image, wherein the first segmented image is derived by performing pore segmentation on the petrographic image with a K-means clustering algorithm;

determine a second microfacies characteristic of the sample based on a second segmented image of the petrographic image, wherein the second segmented image is derived from the petrographic image by semantic segmentation with a K-means clustering algorithm; and determine a third microfacies characteristics of the sample based on a third segmented images of the petrographic images, wherein the third segmented images are derived from by performing semantic segmentation on the petrographic images by a convolutional neural network.

Embodiment 6B. The computer system of 6A, wherein the first microfacies characteristic includes an abundance of allochems (rock grains or particles), grains and allochem grain types, inter-allochems mud-size material particles, the skeletal versus non-skeletal grains ratio, the compaction among grains, the cementation among grains, a grain type, a cement type, a grain radius distribution, a grain size distribution, a grain to inter-grains mud-size material ratio, a cement-to-grain ratio, porosity (e.g., an inter-particle granular porosity, an intra-particle granular porosity, or a porosity value indicative of both), amount of dissolution pores such as vugs, a pore radius distribution, a pore size distribution, the connectivity of pores, amount of fractures, concentration of hydrocarbon, oil saturation, or a combination thereof.

Embodiment 6C. The computer system of 6A or 6B, wherein the K-means clustering algorithm for the pore segmentation is unsupervised, wherein the K-means clustering algorithm for the semantic segmentation is unsupervised, wherein the convolutional neural network algorithm for the semantic segmentation is unsupervised, or a combination thereof.

Embodiment 6D. The computer system of any of 6A to 6C, wherein the instructions cause the one or more computer device to train the convolutional neural network according to a technique disclosed herein.

Embodiment 6E. The computer system of any of 6A to 6D, wherein the instructions cause the second computing device to: post-process a reconstructed petrographic input image provided by the convolutional neural network to produce the third segmented image.

Embodiment 6F. The computer system of 6E, wherein post-process comprises perform a SLIC algorithm and normalized graphic cut technique on the reconstructed petrographic input image.

While embodiments have been shown and described, modifications thereof can be made by one skilled in the art without departing from the spirit and teachings of this disclosure. The embodiments described herein are exemplary only, and are not intended to be limiting. Many variations and modifications of the embodiments disclosed herein are possible and are within the scope of this disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, Rl, and an upper limit, Ru, is disclosed, any number falling within the range is specifically disclosed. In particular, the following numbers within the range are specifically disclosed: R=Rl+k*(Ru-Rl), wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element may be present in some embodiments and not present in other embodiments. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of this disclosure. Thus, the claims are a further description and are an addition to the embodiments of this disclosure. The discussion of a reference herein is not an admission that it is prior art, especially any reference that may have a publication date after the priority date of this application. The disclosures of all patents, patent applications, and publications cited herein are hereby incorporated by reference, to the extent that they provide exemplary, procedural, or other details supplementary to those set forth herein.

What is claimed is:

1. A method for analysis of a petrographic image of a sample of a subterranean formation, the method comprising:
    performing an unsupervised machine-learning algorithm on the petrographic image; and
    determining a microfacies or a microfacies characteristic of the sample based on a segmented image provided by the unsupervised machine-learning algorithm that is performed on the petrographic image,
    wherein performing an unsupervised machine-learning algorithm on the petrographic image comprises:
    performing a K-means clustering algorithm on the petrographic image to produce a segmented petrographic output image having pore regions segmented from matrix regions;
    utilizing a distance transform and a watershed algorithm on the segmented petrographic output image to produce a finalized petrographic output image having the pore regions segmented to into individual pore spaces; and
    producing the segmented image having the pore regions segmented into individual pore spaces and the pore regions segmented from the matrix regions;
    wherein the microfacies characteristic of the sample that is determined is porosity, pore radius distribution, pore size distribution, or a combination thereof.

2. The method of claim 1, wherein the microfacies characteristic is selected from an abundance of allochems, grains and allochem grain types, inter-allochems mud-size material particles, skeletal versus non-skeletal grains ratio, compaction among grains, a cementation among grains, a grain type, a cement type, a grain radius distribution, a grain size distribution, a grain to inter-grains mud-size material ratio, a cement-to-grain ratio, porosity, an amount of dissolution pores, a pore radius distribution, a pore size distribution, a connectivity of pores, amount of fractures, a concentration of hydrocarbon, oil saturation, or a combination thereof.

3. The method of claim 1, wherein performing an unsupervised machine-learning algorithm on the petrographic image comprises:
    performing a K-means clustering algorithm on the petrographic image to identify each pixel in the petrographic image as being part of a grain cluster, a cement cluster, a pore space cluster, or an oil cluster; and
    producing the segmented image based on performing the K-means clustering algorithm; and
    wherein the microfacies characteristic of the sample that is determined is grain radius distribution, grain size distribution, oil saturation, cement-to-grain ratio, or a combination thereof.

4. The method of claim 1, wherein performing an unsupervised machine-learning algorithm on the petrographic image comprises:
    processing the petrographic image by a convolutional neural network to identify each pixel in the petrographic image as a grain type, cement type, a pore space, or oil; and
    producing the segmented image after processing;
    wherein the microfacies characteristic of the sample that is determined is grain type, cement type, fluid type, grain radius distribution, grain size distribution, oil saturation, cement-to-grain ratio, inter-grains micrite mud to grain ratio, or a combination thereof.

5. The method of claim 4, wherein the convolutional neural network has a W-net architecture.

6. The method of claim 4, wherein performing an unsupervised machine-learning algorithm on the petrographic image further comprises:
performing simple linear iterative clustering on a segmented petrographic input image provided by the convolutional neural network to produce superpixels.

7. The method of claim 6, wherein performing an unsupervised machine-learning algorithm on the petrographic image further comprises:
performing a normalized graph cut technique on the superpixels to produce a finalized petrographic output image;
wherein the finalized petrographic output image is used as the final segmented image.

8. The method of claim 4, wherein performing an unsupervised machine-learning algorithm on the petrographic image further comprises:
training the convolutional neural network with petrographic training data, wherein the petrographic training data comprises image training data for a plurality of petrographic training images.

9. The method of claim 8, wherein each of the plurality of petrographic training images has a training pixel resolution, wherein an input pixel resolution of the petrographic image is equal to the training pixel resolution.

10. The method of claim 1, further comprising:
capturing, by an image capture device, the petrographic image of the sample of the subterranean formation.

11. The method of claim 1, further comprising:
drilling, completing, or producing hydrocarbons from a wellbore formed in the subterranean formation based on the microfacies characteristic of the sample that is determined based on the segmented image.

12. The method of claim 1, further comprising:
receiving, by a reservoir modeling computer, the microfacies characteristic of the sample that is determined based on the unsupervised machine-learning algorithm that is performed on the petrographic image; and
modeling, by the reservoir modeling computer, features of at least a portion of the subterranean formation using the microfacies characteristic.

13. A computer system for analysis of a petrographic image of a sample of a subterranean formation, comprising:
a computer device having at least one memory and at least one processor, wherein the at least one memory and the at least one processor are respectively configured to store and execute instructions for causing the computer device to:
perform a machine-learning algorithm on the petrographic image; and
determine a microfacies or a microfacies characteristic of the sample based on a segmented image provided by the machine-learning algorithm,
wherein the machine-learning algorithm is unsupervised and is performed in the convolutional neural network having the W-net architecture, wherein the instructions cause the computer device to:
perform simple linear iterative clustering on a segmented petrographic input image provided by the convolutional neural network to produce superpixels; and
perform a normalized graph cut technique on the superpixels to produce a finalized petrographic output image,
wherein the finalized petrographic output image is used as the final segmented image.

14. The computer system of claim 13, wherein the microfacies characteristic is selected from an abundance of allochems, grains and allochem grain types, inter-allochems mud-size material particles, skeletal versus non-skeletal grains ratio, compaction among grains, a cementation among grains, a grain type, a cement type, a grain radius distribution, a grain size distribution, a grain to inter-grains mud-size material ratio, a cement-to-grain ratio, porosity, an amount of dissolution pores, a pore radius distribution, a pore size distribution, a connectivity of pores, amount of fractures, a concentration of hydrocarbon, oil saturation, or a combination thereof.

15. The computer system of claim 13, further comprising:
an image capture device coupled to the computer device, wherein the image capture device is configured to capture the petrographic image of the sample of the subterranean formation; and
wherein the instructions cause the computer device to:
receive the petrographic image from the image capture device; and
convert the petrographic image into the petrographic image.

16. The computing system of claim 13, further comprising:
a reservoir modeling computer coupled to the computer device and having at least one memory and at least one processor, wherein the at least one memory of the reservoir modeling computer and the at least one processor of the reservoir modeling computer are respectively configured to store and execute instructions for causing the reservoir modeling computer to:
receive, from the computer device, the microfacies characteristic of the sample that is determined based on the segmented image provided by the machine-learning algorithm; and
model features of at least a portion of the subterranean formation using the microfacies characteristic.

17. The computer system of claim 13, wherein the computer device includes a big data platform.

18. A method for analysis of a petrographic image of a sample of a subterranean formation, the method comprising:
performing an unsupervised machine-learning algorithm on the petrographic image; and
determining a microfacies or a microfacies characteristic of the sample based on a segmented image provided by the unsupervised machine-learning algorithm that is performed on the petrographic image,
wherein performing an unsupervised machine-learning algorithm on the petrographic image comprises:
processing the petrographic image by a convolutional neural network to identify each pixel in the petrographic image as a grain type, cement type, a pore space, or oil; and
producing the segmented image after processing;
wherein the microfacies characteristic of the sample that is determined is grain type, cement type, fluid type, grain radius distribution, grain size distribution, oil saturation, cement-to-grain ratio, inter-grains micrite mud to grain ratio, or a combination thereof, and
wherein performing an unsupervised machine-learning algorithm on the petrographic image further comprises:
performing simple linear iterative clustering on a segmented petrographic input image provided by the convolutional neural network to produce superpixels.

19. The method of claim 18, wherein performing an unsupervised machine-learning algorithm on the petrographic image further comprises:
  performing a normalized graph cut technique on the superpixels to produce a finalized petrographic output image;
  wherein the finalized petrographic output image is used as the final segmented image.

20. The method of claim 18, wherein the microfacies characteristic is selected from an abundance of allochems, grains and allochem grain types, inter-allochems mud-size material particles, skeletal versus non-skeletal grains ratio, compaction among grains, a cementation among grains, a grain type, a cement type, a grain radius distribution, a grain size distribution, a grain to inter-grains mud-size material ratio, a cement-to-grain ratio, porosity, an amount of dissolution pores, a pore radius distribution, a pore size distribution, a connectivity of pores, amount of fractures, a concentration of hydrocarbon, oil saturation, or a combination thereof.

21. The method of claim 18, wherein the convolutional neural network has a W-net architecture.

22. The method of claim 18, wherein performing an unsupervised machine-learning algorithm on the petrographic image further comprises:
  training the convolutional neural network with petrographic training data, wherein the petrographic training data comprises image training data for a plurality of petrographic training images.

23. The method of claim 22, wherein each of the plurality of petrographic training images has a training pixel resolution, wherein an input pixel resolution of the petrographic image is equal to the training pixel resolution.

24. The method of claim 18, further comprising:
  capturing, by an image capture device, the petrographic image of the sample of the subterranean formation.

25. The method of claim 18, further comprising:
  drilling, completing, or producing hydrocarbons from a wellbore formed in the subterranean formation based on the microfacies characteristic of the sample that is determined based on the segmented image.

26. The method of claim 18, further comprising:
  receiving, by a reservoir modeling computer, the microfacies characteristic of the sample that is determined based on the unsupervised machine-learning algorithm that is performed on the petrographic image; and
  modeling, by the reservoir modeling computer, features of at least a portion of the subterranean formation using the microfacies characteristic.

* * * * *